(12) United States Patent  (10) Patent No.: US 6,589,226 B1
Owens  (45) Date of Patent: Jul. 8, 2003

(54) CATHETER SHAFT AND METHOD OF MAKING A CATHETER SHAFT

(75) Inventor: Timothy R. Owens, Dublin, CA (US)

(73) Assignee: Advanced Cardiovascular Systems, Inc., Santa Clara, CA (US)

( * ) Notice: Subject to any disclaimer, the term of this patent is extended or adjusted under 35 U.S.C. 154(b) by 125 days.

(21) Appl. No.: 09/693,006

(22) Filed: Oct. 20, 2000

(51) Int. Cl.$^7$ .............................................. A61M 25/00
(52) U.S. Cl. ..................................................... 604/523
(58) Field of Search ............................... 264/340, 320; 604/523, 264

(56) References Cited

U.S. PATENT DOCUMENTS

| | | | |
|---|---|---|---|
| 5,411,477 A | 5/1995 | Saab | 604/96 |
| 5,499,973 A | 3/1996 | Saab | 604/96 |
| 5,507,995 A * | 4/1996 | Schweich et al. | 264/293 |
| 5,902,268 A | 5/1999 | Saab | 604/96 |
| 5,928,191 A * | 7/1999 | Houser et al. | 128/898 |

* cited by examiner

Primary Examiner—Edward K. Look
Assistant Examiner—Kimya N McCoy
(74) Attorney, Agent, or Firm—Fulwider Patton Lee & Utecht, LLP

(57) ABSTRACT

A method of making a catheter having a catheter shaft, the method including axially deflecting at least a section of the catheter shaft. The shaft section is axially deflected in a first radial direction on the shaft circumference one or more times. In a presently preferred embodiment, the method further includes axially deflecting the shaft section in at least a second radial direction on the shaft one or more times. The axial deflection produces stress in at least a section of the polymeric tubular member which reduces the push force of the shaft and catheter. The invention is also directed to a catheter shaft formed using the method of the invention, the catheter shaft generally comprising a polymeric tubular member. The polymeric tubular member has a section with deflection-induced stress from axial deflection of the section, so that the shaft has a push force reduced by the axial deflection-induced stress. In one embodiment, the section of the shaft having axial deflection-induced stress is adjacent to proximal and distal shaft sections which do not have the axial deflection-induced stress. The method of the invention produces a catheter having improved catheter push and trackability due to the reduced push force of the catheter shaft, which reduces bending resistance of the catheter without adversely reducing the pushability of the catheter.

26 Claims, 2 Drawing Sheets

CATHETER SHAFT AND METHOD OF MAKING A CATHETER SHAFT

BACKGROUND OF THE INVENTION

This invention generally relates to medical devices, and particularly to balloon catheters.

In percutaneous transluminal coronary angioplasty (PTCA) procedures, a guiding catheter is advanced until the distal tip of the guiding catheter is seated in the ostium of a desired coronary artery. A guidewire, positioned within an inner lumen of an dilatation catheter, is first advanced out of the distal end of the guiding catheter into the patient's coronary artery until the distal end of the guidewire crosses a lesion to be dilated. Then the dilatation catheter having an inflatable balloon on the distal portion thereof is advanced into the patient's coronary anatomy, over the previously introduced guidewire, until the balloon of the dilatation catheter is properly positioned across the lesion. Once properly positioned, the dilatation balloon is inflated with liquid one or more times to a predetermined size at relatively high pressures (e.g. greater than 8 atmospheres) so that the stenosis is compressed against the arterial wall and the wall expanded to open up the passageway. Generally, the inflated diameter of the balloon is approximately the same diameter as the native diameter of the body lumen being dilated so as to complete the dilatation but not overexpand the artery wall. Substantial, uncontrolled expansion of the balloon against the vessel wall can cause trauma to the vessel wall. After the balloon is finally deflated, blood flow resumes through the dilated artery and the dilatation catheter can be removed therefrom.

In such angioplasty procedures, there may be restenosis of the artery, i.e. reformation of the arterial blockage, which necessitates either another angioplasty procedure, or some other method of repairing or strengthening the dilated area. To reduce the restenosis rate and to strengthen the dilated area, physicians frequently implant an intravascular prosthesis, generally called a stent, inside the artery at the site of the lesion. Stents may also be used to repair vessels having an intimal flap or dissection or to generally strengthen a weakened section of a vessel. Stents are usually delivered to a desired location within a coronary artery in a contracted condition on a balloon of a catheter which is similar in many respects to a balloon angioplasty catheter, and expanded to a larger diameter by expansion of the balloon. The balloon is deflated to remove the catheter and the stent left in place within the artery at the site of the dilated lesion.

An important characteristic of balloon catheters or stent delivery catheters is the transmission of force from the proximal to the distal end of the catheter. This force transmission is generally referred to as catheter push, and significantly affects the physician's ability to direct the catheter distal end into and across a stenosis in a blood vessel by manipulating the proximal end of the catheter outside the patient's blood vessel. In the design of catheters, a tradeoff exists between the competing characteristics of shaft rigidity and flexibility. For example, catheter shafts must have sufficient rigidity to efficiently transmit force to enhance catheter push, in addition to sufficient flexibility to allow the catheter to bend and track within the tortuous body lumen. Catheter shafts which are disadvantageously rigid will resist bending and conforming to tortuous body lumens, which can inhibit catheter push and trackability and cause vessel injury. Consequently, catheter shaft rigidity and bendability must be balance to provide good push and prevent excessive bending resistance. It would be a significant advance to provide a catheter having improved pushability and trackability.

SUMMARY OF THE INVENTION

This invention is directed to a method of making a catheter having a catheter shaft, the method including axially (i.e., longitudinally) deflecting at least a section of the catheter shaft. The shaft section is axially deflected in a first radial direction on the shaft circumference one or more times. In a presently preferred embodiment, the method further includes axially deflecting the shaft section in at least a second radial direction on the shaft one or more times. The axial deflection produces stress in at least a section of the polymeric tubular member which reduces the push force of the shaft and catheter. The invention is also directed to a catheter shaft formed using the method of the invention, the catheter shaft generally comprising a polymeric tubular member. The polymeric tubular member has a section with deflection-induced stress from axial deflection of the section, so that the shaft has a push force reduced by the axial deflection-induced stress. In one embodiment, the section of the shaft having axial deflection-induced stress is adjacent to proximal and distal shaft sections which do not have the axial deflection-induced stress. The method of the invention produces a catheter having improved catheter push and trackability due to the reduced push force of the catheter shaft, which reduces bending resistance of the catheter without adversely reducing the pushability of the catheter. While discussed primarily in terms of a catheter shaft, the invention should be understood to include other catheter components which may be bonded to the catheter shaft, such as a balloon shaft and a soft distal tip.

In one embodiment of the invention, a desired section of the catheter shaft is axially deflected in a manner to produce stress only in the targeted section. Thus, a specific section such as a junction between catheter shaft sections or catheter components is axially deflected according to the method of the invention, to thereby lower the bending resistance at the junction, and preferably without affecting the adjacent sections of the catheter. In one embodiment, the junction has a higher bending resistance than adjacent sections of the catheter shaft before being axially deflected according to the method of the invention. Similarly, a section on the catheter that will be positioned at a specific location within the patient's body lumen during use, such as the aortic arch of the aorta, can be can be axially deflected according to the method of the invention to lower the bending resistance at the section on the catheter shaft, preferably without affecting the adjacent sections of the catheter.

The stress, which in accordance with the invention is induced by axial deflection of the catheter shaft, is reflected in molecular orientation and/or plastic deformation in the catheter shaft. The shaft molecular orientation and/or plastic deformation gives directionality to the material properties of the shaft. For example, the axial deflection according to the method of the invention stretches or strains the shaft in an axial direction, such that the tensile properties of the shaft in a longitudinal direction perpendicular to the direction of the applied force are modified. Specifically, the molecular orientation and/or plastic deformation affects the axial tensile strength and the longitudinal tensile strength of the shaft by stressing the walls of the shaft, and affects the torsional rigidity of the shaft by stressing the material forming the shaft beyond the elastic limit of the material. The stress modifies the material dimensions and elasticity, and will lower tensile and torsional properties, and the modulus of the polymeric shaft. In a presently preferred embodiment, the stress induced molecular orientation and/or plastic deformation produced in the catheter shaft is in a direction aligned with the longitudinal axis of the shaft.

In one embodiment of the invention, the catheter shaft is axially deflected according to the method of the invention after assembly of the various catheter components. Thus, various targeted sections of the catheter, such as a junction between shaft sections, a junction between a shaft section and a distal tip, and a junction between a balloon shaft and the catheter shaft, may be modified according to the method of the invention by axially deflecting the section. Axially deflecting a section of the catheter after assembly of the catheter components according to the method of the invention facilitates determination of the specific location on the catheter shaft where the axial deflection-induced stress is desired. In contrast, if done before catheter assembly, catheter component tolerances and catheter assembly must be carefully controlled in order to assure that the axially deflected section is at the desired longitudinal location on the catheter. Moreover, processes performed during assembly of the catheter, such as fusion bonding of catheter components, may result in a relaxation of the residue of stress, and a loss of the state of molecular orientation and/or plastic deformation, produced by the axial deflection of the catheter components.

The catheter made according to the method of the invention has improved push and lowered bending resistance due to the axial deflection-induced stress. The catheter shaft has deflection induced stress, which is reflected in plastic deformation and/or molecular orientation in the catheter shaft, such that the push force of the shaft is reduced. Moreover, in one embodiment, the axial deflection-induced stress is targeted to a desired location on the shaft for improved catheter performance. These and other advantages of the invention will become more apparent from the following detailed description when taken in conjunction with the accompanying exemplary drawings.

DETAILED DESCRIPTION OF THE INVENTION

Figure 1:
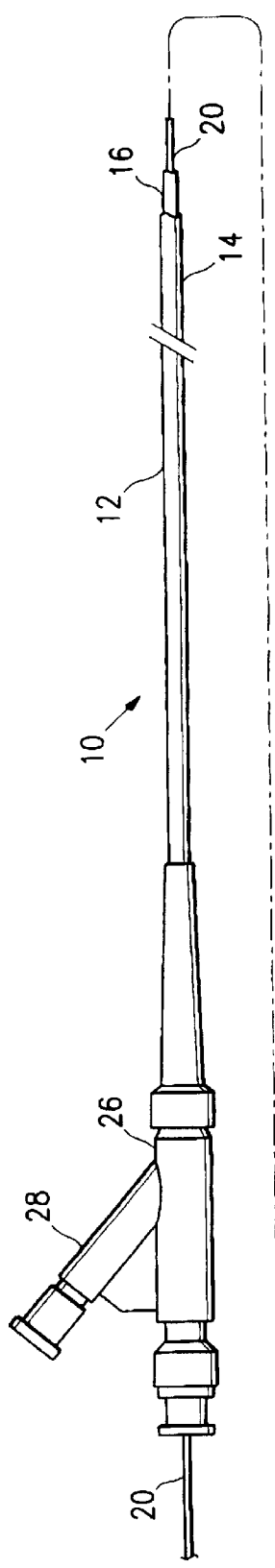
FIG. 1 is an elevational view, partially in section, of a balloon catheter for delivering a stent, that embodies features of the invention.
Figure 2:
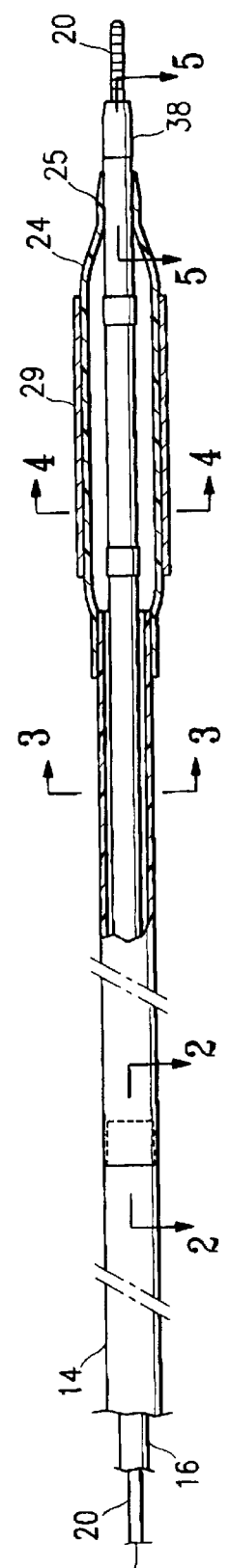
FIG. 2 is an enlarged longitudinal cross sectional view of the catheter shown in FIG. 1, illustrating the junction of the shaft taken along line 2—2.
Figure 3:
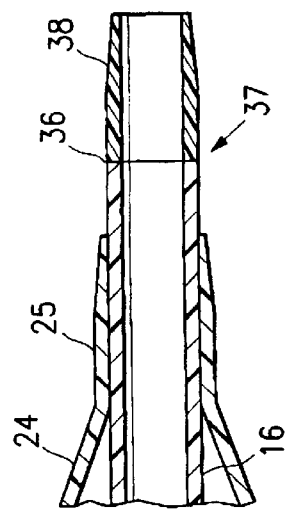
FIG. 3 is a transverse cross-section of the catheter shown in FIG. 1 taken along line 3—3.
Figure 4:
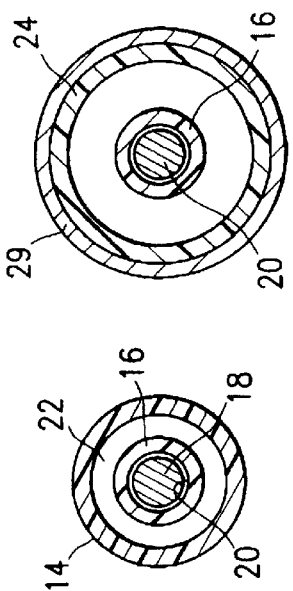
FIG. 4 is a transverse cross-section of the catheter shown in FIG. 1 taken along line 4—4.

FIGS. 1–5 illustrate an over-the-wire type stent delivery balloon catheter 10 embodying features of the invention. Catheter 10 generally comprises an elongated catheter shaft 12 having an outer tubular member 14 and an inner tubular member 16. Inner tubular member 16 defines a guidewire lumen 18 adapted to slidingly receive a guidewire 20. The coaxial relationship between outer tubular member 14 and inner tubular member 16 defines annular inflation lumen 22. An inflatable balloon 24 disposed on a distal section of catheter shaft 12 having a proximal end sealingly secured to the distal end of outer tubular member 14 and a distal end sealingly secured to the distal end of inner tubular member 16 so that its interior is in fluid communication with inflation lumen 22. Expandable tubular stent 29 is mounted on balloon 24. An adapter 26 at the proximal end of catheter shaft 12 is configured to provide access to guidewire lumen 18, and to direct inflation fluid through arm 28 into inflation lumen 22. FIGS. 3 and 4 illustrate transverse cross sectional views of the catheter shown in FIG. 1, taken along lines 3—3 and 4—4, respectively.

In the embodiment illustrated in FIG. 1, outer tubular member 14 comprises a proximal portion 30 secured to a distal portion 32 at a junction 34 between the proximal portion 30 and the distal portion 32. FIG. 2 illustrates an enlarged, longitudinal cross sectional view of the catheter shown in FIG. 1, taken along line 2—2, illustrating the junction 34 between the outer tubular member proximal portion 30 and distal portion 32. In the illustrated embodiment, the junction 34 is a lap joint. However, other suitable junctions may be used including butt joints, tapered joints and the like. The junction 34 is preferably formed by fusion bonding the proximal portion 30 and the distal portion 32 together by heating the polymeric material of the outer tubular member at least at the site of contact between the proximal portion 30 and distal portion 32 so that the polymeric material softens and melts, and allowing the polymeric material to cool, to fuse the two portions together at the junction 34.

Figure 5:
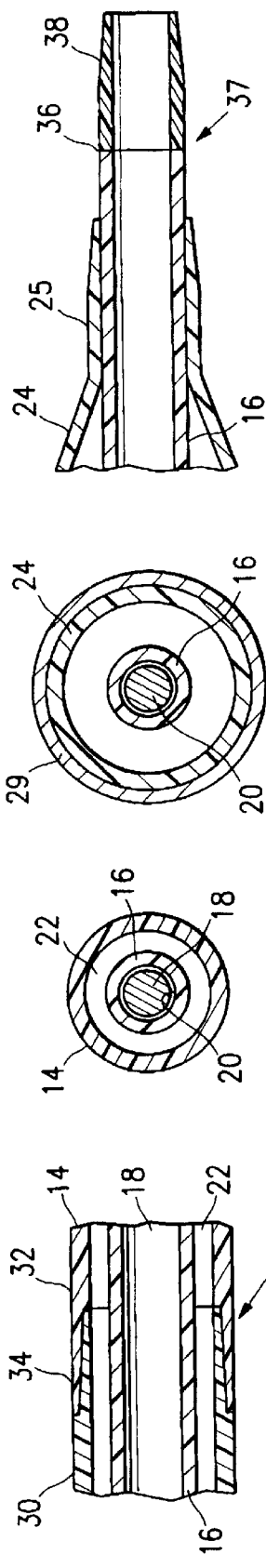
FIG. 5 is an enlarged longitudinal cross sectional view of the catheter shown in FIG. 1, illustrating the junction of the shaft and distal tip taken along line 5—5.

FIG. 5 illustrates a longitudinal cross sectional view of the catheter shown in FIG. 1, taken along line 5—5, illustrating a junction 36 between a distal end of the inner tubular member 16 and a distal tip member 38. In the illustrated embodiment, the junction 36 is a butt joint. However, other suitable junctions may be used including lap joints, tapered joints and the like. In a presently preferred embodiment, junction 36 is formed by fusion bonding as discussed above in relation to junction 34.

In the method of the invention, at least a section of one or more of the polymeric tubular members forming the catheter shaft 12 is axially deflected one or more times to produce stress in the shaft 12. The deflection induced stress reduces the push force of the catheter shaft and is reflected in molecular orientation and/or plastic deformation in the shaft. In a presently preferred embodiment, the shaft is axially deflected about 1 to about 20 times, and preferably about 1 to about 6 times in a given radial direction, depending on the polymeric material forming the catheter shaft and any catheter components secured thereto at the site of axial deflection. In one embodiment, the catheter shaft is repeatedly axially deflected a plurality of times in each particular radial direction of deflection.

In a presently preferred embodiment, the catheter has a push force, i.e., the force required to advance the catheter per push distance, which is reduced by about 5 to about 15 grams, preferably about 8 to about 10 grams, most preferably about 10 grams, due to the axial deflection of the catheter shaft according to the method of the invention. The push force of the catheter before being reduced by the axial deflection is typically about 50 to about 250 grams. The push force of the catheter is measured as is conventionally known in the industry. The push force may be measured using a catheter push test, in which the catheter shaft is placed in a fixture having a path formed therein. As a motor driven roller feeds the catheter shaft through the path, a force transducer measures the force in the opposite direction required to advance the catheter shaft. Similarly, the force transmission of the catheter shaft may be measured as the differential of the force at the distal tip of the catheter shaft and the force at the proximal end of the catheter shaft, as the catheter is advanced through a tortuous path of a fixture. As the catheter shaft is fed in the path of the fixture, a force transducer measures the force at the proximal end of the catheter at the input of the fixture, and the actual force transferred through the catheter is measured by a second transducer at the other end of the catheter shaft in the fixture.

In one embodiment, a targeted section of the catheter shaft 12 is axially deflected according to the method of the invention. The targeted section may be a variety of desired locations on the catheter, such as targeted section 35 which includes at least junction 34 between proximal portion 30 and distal portion 32 of the outer tubular member, and may include catheter shaft sections on one or both side of the junction in addition to the junction 34, as illustrated in FIG. 2. Similarly, targeted section 37 includes at least junction 36 between inner tubular member 16 and distal tip 38, as illustrated in FIG. 5. In a presently preferred embodiment, junctions 34 and 36 are fusion bonds, which will not be adversely weakened by the radial deflection. However, in alternative embodiments, junctions 34 and 36 may include an adhesive bond, provided the bond is not adversely weakened by the radial deflection. In an alternative embodiment, the targeted section is in a section of the catheter shaft which is positioned in a specific location of the patient's vascular anatomy during a medical procedure, such as a bend or turn in a coronary artery.

Figure 6:
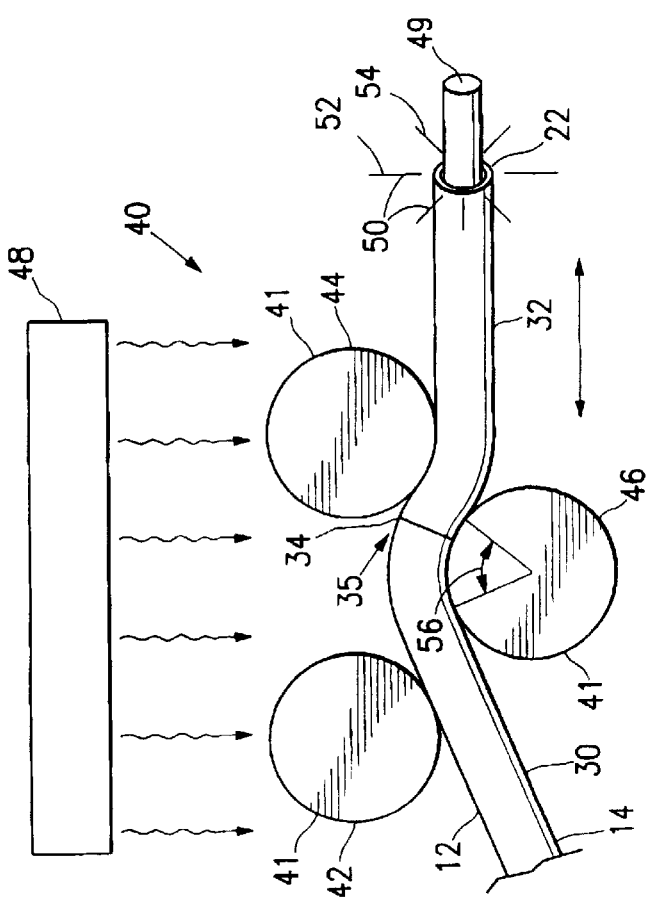
FIG. 6 is an elevational view of the catheter shaft in a axial deflection assembly which embodies features of the invention, during axial deflection of a section of the shaft at the junction between two shaft sections of the outer tubular member according to a method which embodies features of the invention.

FIG. 6 illustrates the catheter 10 with a section of shaft 12 in place in a radial deflection apparatus 40 which embodies features of the invention. In the embodiment illustrated in FIG. 6, axial deflection apparatus generally comprises rotating members 41, such as wheels or cams, which rotate to produce motion in the catheter shaft. In the illustrated embodiment, three rotating members 41 rotate clockwise and counter clockwise to produce reciprocating longitudinal motion in the catheter shaft 12 which is placed between the rotating members. Although three rotating members 41 are illustrated in FIG. 6, in alternative embodiments, one, two or more than three rotating members may be used. First rotating member 42 and second rotating member 44 are longitudinally aligned, and third rotating member 46 is between and radially offset from the first and second rotating members 42/44. The shaft 12 has an outer diameter which is larger than the radial distance between the third rotating member 46 and the first and second rotating members 42/44, such that the section 35 of the shaft 12, placed between the rotating members 41 as illustrated, is deflected or bent away from the longitudinal axis of the shaft proximal to the section 35. Thus, rotating one or more of the members 41 clockwise and counter clockwise advances targeted section 35 into an axially deflected configuration and withdraws the section 35 out of the axially deflected configuration, to thereby repeatedly axially deflect the section 35 of the shaft 12. The axial deflection angle 56, i.e., the angle between the points on the catheter shaft where the shaft first comes into contact with the rotating member 46 and thereafter first separates from contact with the rotating member 46, is illustrated in FIG. 6. In a presently preferred embodiment, the contact angle of deflection 56 is about 20 to about 120 degrees, preferably about 50 to about 70 degrees, around a cam 46 diameter of about 0.125 inch to about 2 inch, preferably about 0.375 inch to about 1 inch. As illustrated by FIG. 6, the axial deflection of the method of the invention bends the shaft such that a side of the shaft 12 on the outer side of the bend is stretched as a result of the bending.

Apparatus 40 may include a heat source 48, which elevates the temperature of the shaft 12 during the axial deflection of the shaft. In one embodiment, the shaft section is heated to an elevated temperature of about equal to the softening temperature or glass transition temperature of the polymeric material of the shaft 12. Alternatively, the shaft section is preferably cooled to below ambient temperature if the polymeric material forming the shaft section is highly elastic, to facilitate straining the material to produce axial deflection-induced stress according to the method of the invention. The shaft section is at about 17° C. to about 80° C. during the axial deflection. In one embodiment, the shaft section is at about ambient (room) temperature or about 30° C. during the axial deflection.

As illustrated in FIG. 6, a mandrel 49 is in the lumen 22 of the outer tubular member 14 during radial deflection thereof, although in alternative embodiments, a mandrel is not provided in the shaft lumen during radial deflection of the shaft. Mandrel 49 supports the outer tubular member 14 during the radial deflection to prevent or inhibit kinking thereof and to distribute force, and is typically formed of a flexible polymer or metal such as NiTi alloy.

In a presently preferred embodiment, the shaft 12 is axially deflected in a first radial direction one or more times, and then axially deflected in at least a second radial direction different from the first radial direction one or more times. In FIG. 6, radial direction lines 50 illustrate a plurality of radial directions of the axial deflection, including first 52 and second 54 radial directions. Thus, the catheter shaft 12 is axially deflected a number of times in the first radial direction by longitudinally advancing and withdrawing the catheter shaft 12, the catheter is rotated to change the radial direction of deflection to a second radial direction and the axial deflection cycles are repeated, and the process is repeated the desired number of times. In one embodiment, the shaft 12 is axially deflected in a plurality of radial directions which extend around the circumference of the shaft 12, as illustrated by the radial direction lines 50 in FIG. 6.

In FIG. 6, targeted section 35 which comprises at least junction 34 between the proximal portion 30 and distal portion 32 of outer tubular member is being axially deflected in the axial deflection apparatus 40. In one embodiment of the invention, apparatus 40 is configured to allow axial deflection of a selected targeted section of the shaft, without requiring axial deflection in other sections of the shaft. For example, in the embodiment illustrated in FIG. 6, one or more of the rotating members 41 may be displaceable out of the location illustrated in FIG. 6, to allow the shaft to be place between the rotating members, and then the rotating members moved together into the positions illustrated in FIG. 6 to bend the shaft 12. In the embodiment illustrated in FIG. 6, the targeted section 35 of outer tubular member 14 is axially deflected before the inner tubular member is placed therein to complete assembly of the catheter. However, in alternative embodiments, the inner tubular member 16 is within the lumen 22 of the outer tubular member 14, and a mandrel 49 is within the inner tubular member and/or outer tubular member, during the axial deflection of targeted section 35 of outer tubular member 14.

Figure 8:
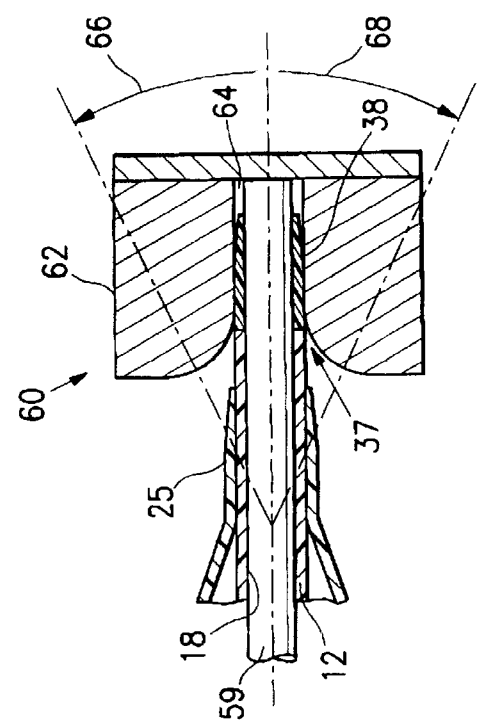
FIG. 8 is an enlarged longitudinal cross sectional view of the distal end of the catheter shown in FIG. 7 in a axial deflection assembly which embodies features of the invention, for axially deflecting the shaft at the junction between the inner tubular member and the distal tip according to a method which embodies features of the invention.
Figure 7:
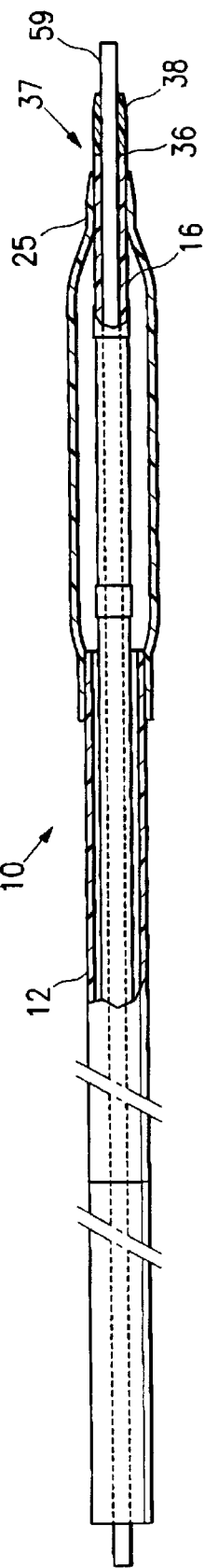
FIG. 7 is an elevational view, partially in section, of the balloon catheter shown in FIG. 1, illustrating a mandrel in the inner tubular member in preparation for axially deflecting the shaft at the junction between the inner tubular member and the distal tip according to a method which embodies features of the invention

FIGS. 7 and 8 illustrate another embodiment of the method of the invention in which the targeted section 37 comprising at least the junction 36 between the inner tubular member 16 and the distal tip 38 is axially deflected one or more times at one or more radial directions around the circumference of the shaft 12. FIGS. 7 and 8 illustrate the catheter 10 with a mandrel 59 in the guidewire lumen 18 defined by the inner tubular member 16 and distal tip 38, to support the inner tubular member 16 and distal tip 38 during axial deflection. FIG. 8 illustrates the distal end of the catheter 10 in a axial deflection apparatus 60 generally comprising a body 62 having a chamber 64 therein configured to receive at least the distal end of the shaft 12 therein. The body 62 is configured to tilt up and/or down relative to the longitudinal axis of the body, through angle 66 and/or angle 68, to axially deflect the targeted section 37 about the axis of the body 62. After section 37 is axially deflected one or more times, the shaft 12 can be rotated, and the axial deflection repeated, as discussed above in relation to the embodiment of FIG. 6 to axially deflect the shaft in radial directions different from the first radial direction. In the embodiment where the body 62 tilts up and down relative to the longitudinal axis of the body 62, the shaft 12 is axially deflected in a first and a second radial direction without having to rotate the shaft 12 within the chamber 64 of the body 62. Although the embodiment of FIG. 8 illustrates the axial deflection of the targeted section 37, in alternative embodiments, the section of the shaft 12 bonded to the balloon shafts, such as the section of the inner tubular member fused or otherwise bonded to the distal balloon shaft 25, may be axially deflected according to the method of the invention to improve the push and bending resistance of the shaft at the location of the distal balloon shaft 25, as discussed herein.

The polymeric materials used to form the catheter shaft or other components axially deflected according to the method of the invention, typically have a crystallinity before the axial deflection of about 10% to about 90%, preferably about 15% to about 80%. In one embodiment of the invention the shaft is axially deflected such that stress induced crystallization is produced in the axially deflected shaft section. The stress induced crystallization typically increases the crystallinity of the catheter component by about 0% to about 100% in the region of the axial deflection.

Inner tubular member 16 and outer tubular member 14 can be formed by conventional techniques, for example by extruding, from materials already found useful in intravascular catheters such a polyethylene, polyvinyl chloride, polyesters, polyamides, polyimides and composite materials. Presently preferred polymeric materials used to form the shaft sections which are axially deflected according to the method of the invention are polyamides such as nylon 12, polyamide block copolymers, polyetheretherketone, polyolefins such as polyethylene, and high density polyethylene. In one embodiment, distal tip member 38 is softer than the inner tubular member 16, and may be formed of soft polymeric materials having a relatively low Shore Durometer hardness, such as about 40 D to 60 D, or by other methods well known in construction of catheter soft distal tips. The various components may be joined by heat bonding or use of adhesives.

The dimensions of catheter 10 are determined largely by the size of the guidewires to be employed and the size of the artery or other body lumen through which the catheter must pass or the size of the stent being delivered. Typically, the outer tubular member 14 has an outer diameter of about 0.02 to about 0.04 inch (0.05 to 0.10 cm), usually about 0.037 inch (0.094 cm), an inner diameter of about 0.015 to about 0.035 inch (0.038 to 0.089 cm), usually about 0.02 inch (0.051 cm). The wall thickness of the outer tubular member 14 can vary from about 0.002 to about 0.008 inch (0.0051 to 0.0201 cm), typically about 0.003 inch (0.0076 cm). The inner tubular member 16 typically has an outer diameter of about 0.012 to about 0.016 inch (0.030 to 0.041 cm), usually about 0.014 inch (0.036 cm). The overall working length of the catheter 10 may range from about 100 to about 150 cm, and is typically about 135 cm. Preferably, balloon 24 may have a length about 0.5 cm to about 4 cm and typically about 2 cm with an inflated working diameter of about 1 to about 8 mm.

The balloon catheter illustrated in FIG. 1 is an over-the-wire catheter. However, various balloon catheter designs may be used, such as rapid exchange and fixed wire catheters. Rapid exchange catheters typically comprise an elongated shaft with a proximal end, a distal end, a balloon on a distal shaft section in fluid communication with an inflation lumen, a distal guidewire port in the distal end of the catheter, a proximal guidewire port spaced a substantial distance from the proximal end of the catheter so that the proximal guidewire port is closer to the distal end than to the proximal end of the catheter, and a short guidewire lumen extending between the proximal and distal guidewire ports.

While the present invention is described herein in terms of certain preferred embodiments, those skilled in the art will recognize that various modifications and improvements may be made to the invention without departing from the scope thereof. For example, in the embodiment illustrated in FIG. 1, the catheter is a stent delivery catheter. However, one of skill in the art will readily recognize that a variety of intravascular catheters may be made according to the method of the invention, such as over-the-wire and rapid exchange type dilatation catheters, guiding catheters, and the like. Although individual features of one embodiment of the invention may be discussed or shown in the drawings in relation to one embodiment and not in other embodiments, individual features of one embodiment may be combined with one or more features of another embodiment or features from a plurality of embodiments.

What is claimed is:

1. A method of making a catheter having a shaft comprising a polymeric tubular member, the method comprising pre-stressing a targeted section of the polymeric tubular member after assembly of said tubular member and prior to use of said catheter so as to modify the material properties thereof, by axially deflecting the targeted section of the polymeric tubular member in a first radial direction one or more times, so that the axial deflection pre-stresses the targeted section of the polymeric tubular member so as to reduce the catheter push force upon use thereof.

2. The method of claim 1 wherein the push force of the catheter is reduced by about 5 to about 15 grams.

3. The method of claim 1 wherein axially deflecting the polymeric tubular member includes producing molecular orientation aligned with a longitudinal axis of the polymeric tubular member.

4. The method of claim 1 wherein axially deflecting the polymeric tubular member includes producing plastic deformation in the polymeric tubular member.

5. The method of claim 1 wherein axially deflecting the polymeric tubular member comprises axially deflecting a targeted portion of the polymeric tubular member, the portion of the tubular member comprising a junction between a first shaft section and a second shaft section which has a length less than a length of the polymeric tubular member.

6. The method of claim 5 including fusion bonding the first and second shaft sections together to form the junction therebetween before axially deflecting the targeted section.

7. The method of claim 5 wherein the second shaft section comprises a distal tip and wherein axially deflecting the targeted section comprises axially deflecting the junction between the first shaft section and the distal tip bonded to the first shaft section.

8. The method of claim 5 wherein the targeted section is adjacent a proximal shaft portion, and wherein axially deflecting the polymeric tubular member comprises axially deflecting only the targeted section, to produce a catheter shaft with the targeted section having deflection induced stress and with the proximal shaft portion not having deflection induced stress.

9. The method of claim 1 including axially deflecting the section of the polymeric tubular member in at least a second radial direction different from the first radial direction one or more times.

10. The method of claim 1 including axially deflecting the polymeric tubular member at a plurality of radial directions which extend around the circumference of the polymer tubular member.

11. The method of claim 1 wherein a mandrel is in a lumen of the polymeric tubular member during the axial deflection, so that axially deflecting the polymeric tubular member includes axially deflecting at least a section of the mandrel therein.

12. The method of claim 1 including axially deflecting the section of the polymeric tubular member in the first direction 1 to 20 times.

13. The method of claim 1 wherein the polymeric tubular member is axially deflected at a contact angle of about 20 to about 180 degrees.

14. The method of claim 1 wherein the polymeric tubular member is axially deflected at a contact angle of about 50 to about 70 degrees.

15. The method of claim 1 wherein axially deflecting the polymeric tubular member includes
  a) placing the polymeric tubular member adjacent to one or more rotating members; and
  b) rotating the rotating members to produce reciprocating longitudinal motion in the polymeric tubular member which advances a section of the polymeric tubular member into a axially deflected configuration and withdraws the section of the polymeric tubular member out of the axially deflected configuration, to repeatedly axially deflect only the section of the polymeric tubular member.

16. The method of claim 5 including heating at least the targeted portion of the polymeric tubular member and axially deflecting the targeted portion of the polymeric tubular member at an elevated temperature.

17. The method of claim 5 including cooling at least the targeted portion of the polymeric tubular member and axially deflecting the targeted portion of the polymeric tubular member at a temperature below ambient temperature.

18. The method of claim 1 wherein axially deflecting the polymeric tubular member includes producing stress induced crystallization in the radially deflected section.

19. The method of claim 1 wherein axially deflecting the polymeric tubular member includes stressing the polymeric tubular member beyond an elastic limit of the polymer.

20. The method of claim 1 wherein axially deflecting the polymeric tubular member includes stressing the polymeric tubular member below an elastic limit of the polymer.

21. A catheter, comprising:
  a polymeric elongated shaft having a proximal end, a distal end, at least one lumen therein, and a targeted section which has been pre-stressed by axial deflection thereof in a first radial direction one or more times so as to modify the material properties thereof to thereby reduce the bending resistance of said targeted section and the push force of the shaft.

22. The catheter of claim 21 wherein the shaft has a push forced reduced by about 5 to about 15 grams.

23. The catheter of claim 21 wherein the section having axial deflection-induced stress comprises a targeted section which includes a fused junction between a first and a second shaft section.

24. The catheter of claim 21 wherein the targeted section has a length which is about 0.75% to about 10% of a length of the shaft.

25. A catheter, comprising
  a) a polymeric elongated shaft having a proximal end, a distal end, at least one lumen therein, the elongated shaft comprising a proximal shaft section, and a distal tip section fusion bonded to the proximal shaft section, and a targeted section between the proximal shaft section and the distal tip section which includes a fusion bonded junction between the proximal shaft section and distal tip shaft section, the targeted section having deflection-induced stress from axial deflection of the targeted section, and the shaft having reduced push force from the axial deflection of the targeted section.

26. The catheter of claim 25 wherein the catheter is a balloon catheter.

* * * * *